United States Patent
Fecht et al.

(10) Patent No.: US 6,432,053 B1
(45) Date of Patent: Aug. 13, 2002

(54) PROCESS FOR NON-INVASIVELY DETERMINING THE DIMENSIONS OF A LESION

(75) Inventors: Barbara A. Fecht; Ronald L. Shelby; Jerod O. Shelby, all of Richland, WA (US)

(73) Assignee: Advanced Diagnostics, Inc., Richland, WA (US)

( * ) Notice: Subject to any disclaimer, the term of this patent is extended or adjusted under 35 U.S.C. 154(b) by 0 days.

(21) Appl. No.: 09/507,559

(22) Filed: Feb. 18, 2000

(51) Int. Cl.[7] ................................................. A61B 8/00
(52) U.S. Cl. ......................................... 600/437; 600/443
(58) Field of Search ................................. 382/132, 133, 382/134; 606/46–47; 600/443, 447, 437

(56) References Cited

U.S. PATENT DOCUMENTS

| | | | |
|---|---|---|---|
| 4,662,222 A | 5/1987 | Johnson | 73/602 |
| 5,179,455 A | 1/1993 | Garlick | 359/9 |
| 5,212,571 A | 5/1993 | Garlick et al. | 359/9 |
| 5,235,553 A | 8/1993 | Garlick et al. | 367/7 |
| 5,329,202 A | 7/1994 | Garlick et al. | 310/334 |
| 5,329,817 A | 7/1994 | Garlick et al. | 73/605 |
| 5,740,268 A * | 4/1998 | Nishikawa et al. | 382/132 |
| 5,984,870 A * | 11/1999 | Giger et al. | 600/443 |
| 5,999,836 A | 12/1999 | Nelson et al. | 600/407 |
| 6,032,673 A * | 3/2000 | Savage et al. | 606/46 |

\* cited by examiner

Primary Examiner—Marvin M. Lateef
Assistant Examiner—Maulin Patel
(74) Attorney, Agent, or Firm—Michael J. Donohue; Seed IP Law Group PLLC

(57) ABSTRACT

There is disclosed a method for non-invasively determining dimensions of a lesion within soft tissue, comprising:

(a) ultrasonically imaging soft tissue in an apparatus having an acoustic transducer, an acoustic focussing system, a holographic imaging detector, and a means for visualizing the holographic image;

(b) obtaining a holographic planar image of a lesion in a first plane having a thickness z and having a dimension across a wide area of the lesion of x and a length across the lesion of y wherein y is at an approximately 90 degree angle to x;

(c) determining if the image of the lesion is contained in different planar images;

(d) measuring the x and y dimensions of the lesion in the plane having the largest sum of x plus y dimensions; and (e) determining the 3-dimensional size with a means for z-axis measurement.

11 Claims, 8 Drawing Sheets

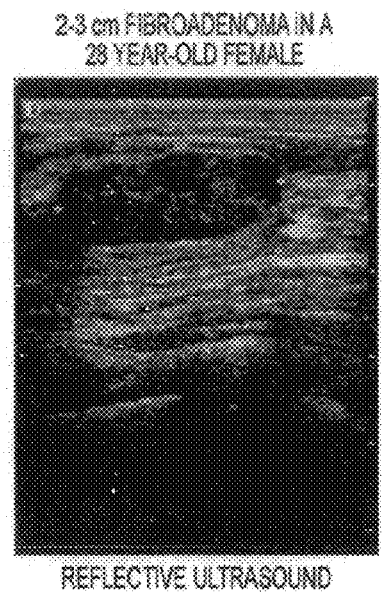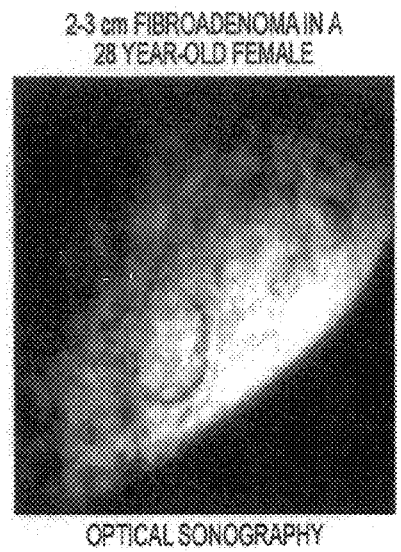
*Fig. 3D*  *Fig. 3E*  *Fig. 3F*

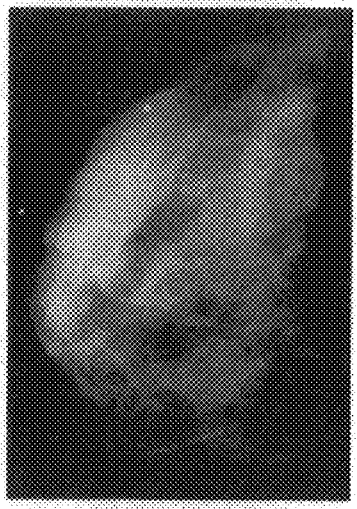
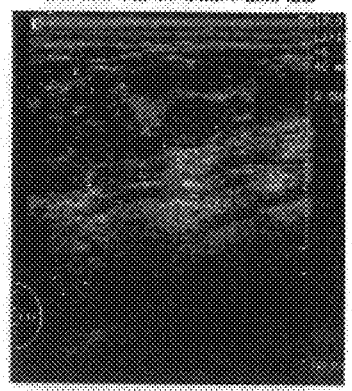
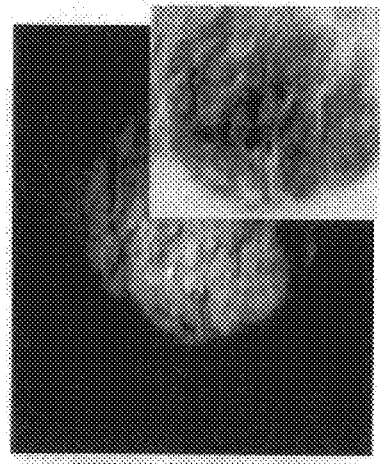
*Fig. 4D*  *Fig. 4E*  *Fig. 4F*

PROCESS FOR NON-INVASIVELY DETERMINING THE DIMENSIONS OF A LESION

TECHNICAL FIELD OF THE INVENTION

The present invention provides a method for non-invasively determining dimensions of a lesion within soft tissue. Specifically, the present invention provides a transmissive ultrasound system having a holographic imaging detector.

BACKGROUND OF THE INVENTION

Breast cancer screening techniques have been limited to mammography because screening techniques need to be economical in order to achieve widespread use. However, mammography often has a high incidence of false positive readings that often prove to be benign or fluid-filled cysts that do not require surgical intervention or other highly invasive therapeutic procedures. It is widely-accepted that late-stage breast cancer detection is associated with significantly increased morbidity and mortality. Despite extensive research, new diagnostic classification systems and improved detection methodologies, there is still a great need to detect small neoplasms (typically 5 mm or smaller) accurately, quickly, non-invasively and inexpensively and with a good idea of size during the early detection process. Failure to detect such early breast cancers is associated with more invasive therapeutic interventions at higher risk and higher expense.

X-Ray mammography is the accepted standard screening tool for diagnosis of breast cancer. It has good resolution and clarity, is capable of detecting microcalcifications and sometimes delineates the borders of some masses. However, 60–80% of subsequent biopsies recommended from mammography result in benign diagnoses. Thus, there is a need in the art to improve the positive predictive value of conventional breast imaging.

Mammography is also less sensitive for detecting cancers in women with mammographically dense breast tissue. Since the more dense, fibrous tissue can obscure neoplasms, mammograms are often inconclusive or inaccurate in these women. Thus, there is a need in the art to more accurately detect neoplasms in women with dense breasts.

In addition, mammography is an invasive procedure that should not be done too frequently in view of a cumulative effect of radiation doses. Many women are hesitant to be imaged because of a risk or even a perceived risk associated with exposures to radiation. Moreover, there is significant discomfort associated with a mammography procedure because the breasts have to under go significant compression that can also distort lesions, if present and flexible. Therefore, there are some significant shortcomings to mammography as a standard means for breast cancer screening.

One alternative to X-Ray mammography is conventional, reflective ultrasound using a pulse-echo technique. Generally, breast sonograms using reflective ultrasound are used to characterize masses (such as whether they are cystic or solid) detected by physical exam or by mammography. There is still debate within this field whether reflective ultrasound is able to predict benign from malignant solid masses. Moreover, reflective ultrasound is operator-dependent, time-consuming, and a full image of the breast cannot be obtained or even stored for later reference. Further, sonography is not useful for the assessment or detection of microcalcifications, often the only sign of early in situ ductal carcinomas.

Therefore, there is a need in the art to overcome these problems associated with early screening of breast cancers and obtain more information and more reliable information, such as lesion size if one is found, from the early screening procedure to better guide follow up and to relieve the extreme anxiety of patients who have something found but have a greater than 50% chance that it is benign or nothing, but is learned days or weeks later. Thus there is a need for more statistically reliable information, such as lesion dimensions, to be obtained during the early and non-invasive screening process and not be determined during follow up procedures which are usually invasive. During initial comparative procedures with mammography and reflective ultrasound, the present procedure of transmissive ultrasound was surprisingly found to not only identify lesions with better accuracy and visualization than either of the other two imaging modalities but also more accurately determine lesion dimensions, a surprising result.

SUMMARY OF THE INVENTION

The present invention provides a method for non-invasively determining dimensions of a lesion within a soft tissue object, comprising:

(a) ultrasonically imaging the object in an apparatus having an acoustic transducer, an acoustic focussing system, a holographic imaging detector, and a means for visualizing the holographic image;

(b) obtaining a holographic planar image of a lesion in a first plane having a thickness z and having a dimension across a wide area of the lesion of x and a length across the lesion of y wherein y is at an approximately 90 degree angle to x;

(c) determining if the image of the lesion within the object is contained in different planar images;

(d) measuring the x and y dimensions of the lesion in the plane having the largest sum of x plus y dimensions; and (e) determining the 3-dimensional size with a means for z-axis measurement.

Preferably, the object is breast tissue. Preferably, the holographic planar image of a lesion in the first plane in step (b) uses all three axes to be orthogonal. Preferably, the apparatus contains a holographic detector element for imaging in an optical mode the distortions cause by transmissive acoustic through the soft tissue. Preferably, the means for z-axis measurement is to either determine numbers of planes traversed of a known thickness, or rotating the object (patient or body segment) such that the z-axis becomes a third dimension with an additional x-y axis measurement at about 90 degrees rotation, or both.

The present invention further provides a method for guiding a biopsy device in soft tissue to a lesion, comprising ultrasonically imaging the soft tissue in an apparatus having an acoustic transducer, an acoustic focussing system, a holographic imaging detector, and a means for visualizing the holographic image to simultaneously visualize both the biopsy device and the lesion site. Preferably, the apparatus contains a holographic detector element for imaging in an optical mode the distortions cause by transmissive acoustic through the soft tissue.

DETAILED DESCRIPTION OF THE INVENTION

Figure 1:
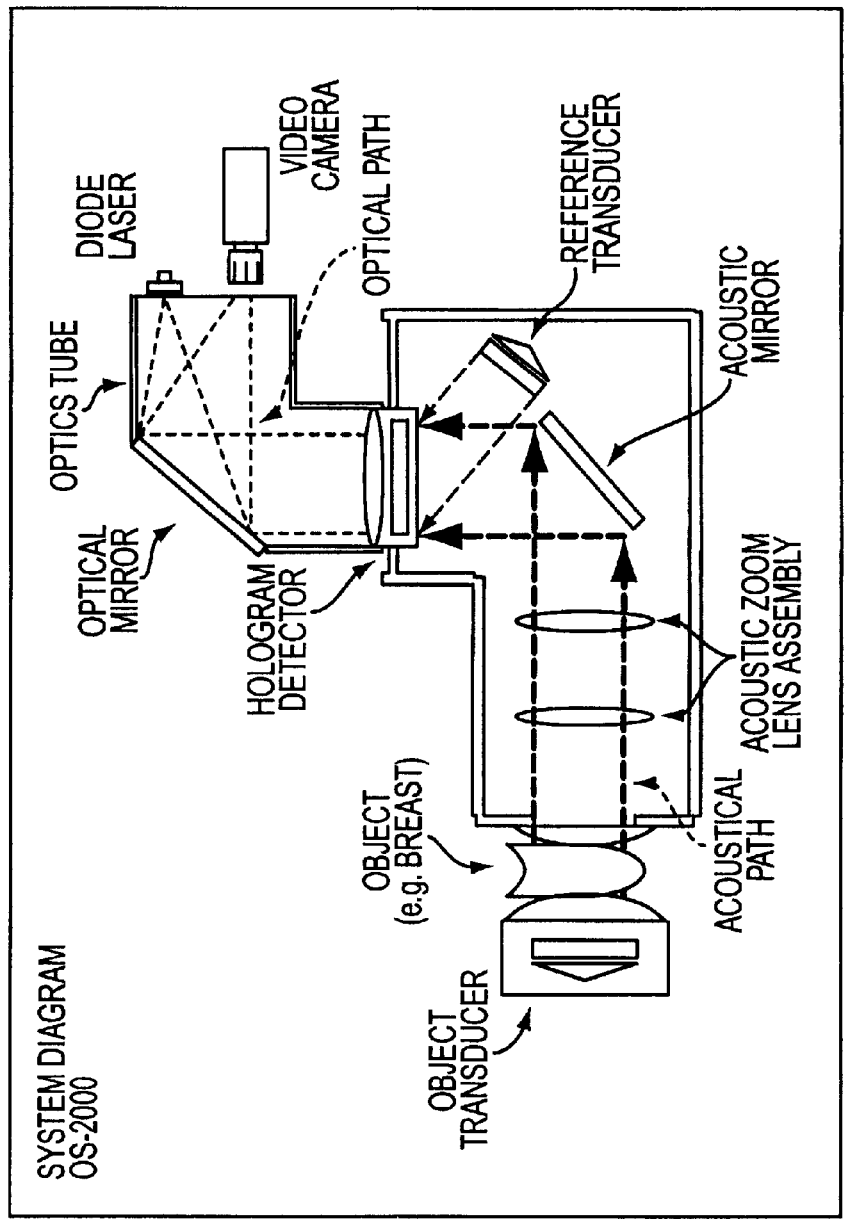
FIG. 1 shows a schematic of the transmissive ultrasound apparatus used having a hologram detector element for visualizing the planar breast images.
Figure 2A:
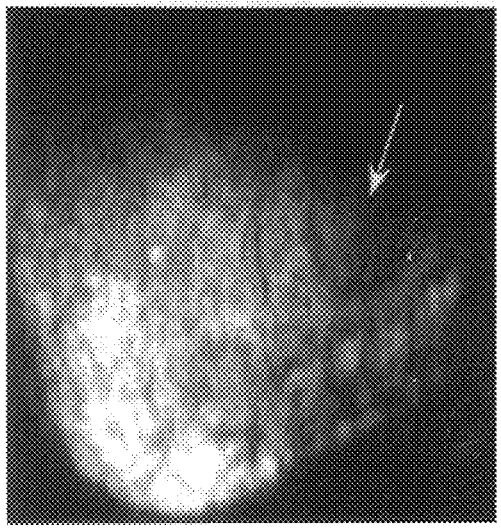
FIG. 2 shows four images of breast tissue using transmissive ultrasound with holographic detection. The top two images show two views of a 2–3 cm infiltrating ductal carcinoma in a 38 year old female. In this mammographically occult cancer, determination of the extent of the tumor with traditional ultrasound (reflective ultrasound) predicted a 9 mm diameter mass. Transmissive ultrasound determined the size to be at least 2.3 cm with a portion of the lesion not included within the field of view. Pathologic examination of the surgically-excised tumor revealed a 2.7 cm diameter invasive carcinoma. The arrows show the lesion in each image. The lower left image shows a 3–4 cm hypodense macrolobular carcinoma in a 44 year old female, as pointed by the arrow. The lower right image shows a retroareolar carcinoma in a 50 year old female. The size of this cancer was also predicted more accurately using transmissive ultrasound imaging.
Figure 2B:
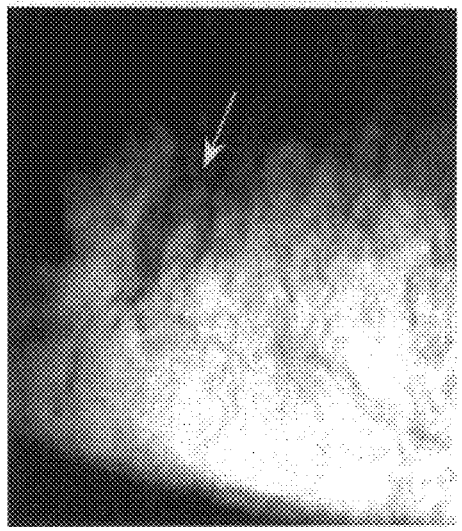
Figure 2C:
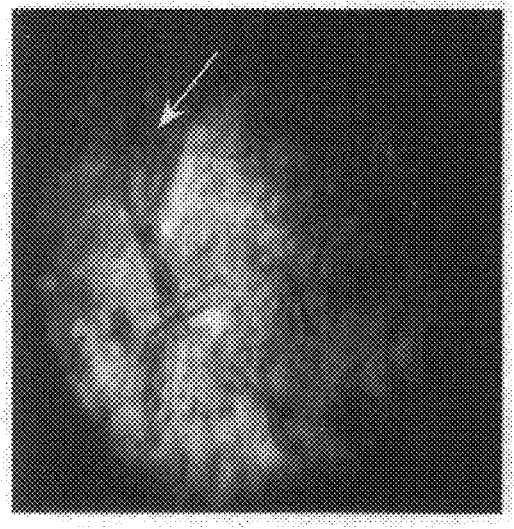
Figure 2D:
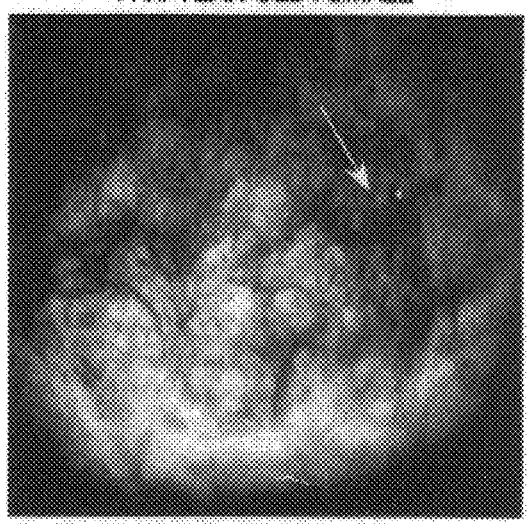

The present invention provides a method for non-invasively determining dimensions of a lesion within soft tissue, comprising:

(a) ultrasonically imaging soft tissue in an apparatus having an acoustic transducer, an acoustic focussing system, a holographic imaging detector, and a means for visualizing the holographic image;

(b) obtaining a holographic planar image of a lesion in a first plane having a thickness z and having a dimension across a wide area of the lesion of x and a length across the lesion of y wherein y is at an approximately 90 degree angle to x;

(c) determining if the image of the lesion is contained in different planar images;

(d) measuring the x and y dimensions of the lesion in the plane having the largest sum of x plus y dimensions; and (e) determining the 3-dimensional size with a means for z-axis measurement.

Preferably, the object is breast tissue. Preferably, the holographic planar image of a lesion in the first plane in step (b) uses all three axes to be orthogonal. Preferably, the apparatus contains a holographic detector element for imaging in an optical mode the distortions cause by transmissive acoustic through the soft tissue. Preferably, the means for z-axis measurement is to either determine numbers of planes traversed of a known thickness, or rotating the object (patient or body segment) such that the z-axis becomes a third dimension with an additional x-y axis measurement at about 90 degrees rotation, or both.

The present invention was made based upon comparison of data for breast screening comparing a transmissive ultrasonography process with holographic imaging to standard X-Ray mammography and, in some instances, standard reflective ultrasound in those breasts where some kind of a lesion was noted by either mammography or reflective ultrasound. Forty-one asymptomatic and symptomatic women ranging in age from 18–83 years were evaluated with transmissive ultrasound and mammography and possibly reflective ultrasound to evaluate transmissive ultrasound with holographic image detection as a modality for detection of breast disease (soft tissue) and possibly characterization. What became surprising was not only the ability to detect lesions as well as or perhaps better than mammography but the ability to characterize the lesions. Particularly these data showed an ability of transmissive ultrasound with holography detection to accurately determine lesion size non-invasively in a manner surprisingly better than mammography or reflective ultrasound. This was confirmed in several cases by subsequent pathology analysis after surgical intervention (when warranted). The margins of lesions were particularly well-defined and provided substantial contrast to fatty and dense parenchyma. The ability to determine tumor extent or lesion size of transmissive ultrasound with holographic detection (also called acoustic holography) was compared to mammography and pulse-echo sonography (reflective ultrasound) and the definitive determination of tumor size was later made after surgical intervention and retrospectively compared to the images (before surgery) obtained and the extent of tumor they predicted. In addition, the present method of transmissive ultrasound was found to better guide biopsy devices (i.e., needles) through non-invasive, real time imaging of soft tissue.

It is well-known that the extent of tumor tissue cannot be accurately or consistently predicted from a mammogram or a traditional reflective ultrasound imaging. Therefore, for many patients, there is no reliable information, prior to surgery, to determine whether a procedure should be a lumpectomy or a mastectomy and repeat surgical procedures are often needed once an accurate determination to tumor stage is made by pathology after the first surgery. The need for repeated surgical procedures adds significantly to the cost of breast cancer treatment and is also much more invasive for the patient, especially those patients thinking that lumpectomy is sufficient until more detailed information is received (post-surgically) indicating that mastectomy was preferred. For this reason, it is particularly important to non-invasively determine and assess tumor extent (or size) to guide the surgical decision before the surgery rather than after a surgery was completed. Such information can also guide biopsy decisions, as well as literally guide a biopsy procedure in real time.

There are several means for imaging in a three-dimensional or z-axis basis. These include a simple 90 degree rotation of the object such that the former z-axis becomes the x or y axis in a subsequent image. In addition, one can stack processed (i.e, visually or computationally) planar images to delineate the dimensions of a lesion along a z-axis. Preferably, using a stacked planar image process, one can use a three dimensional viewing technique to view the stacked images in a virtual reality environment. One such technique, for example, utilizes an Immersadesk™ system (developed at the Electronic Visualization Laboratory of the University of Illinois at Chicago, www.evl.uic.edu/EVL/VR) for three dimensional image viewing (with appropriate stereo glasses).

The data for the 41 patient breast imaging study, wherein breast tissue is a soft tissue, provided high resolution images from transmissive ultrasound with holography detection while overcoming some of the limitations of other imaging modalities (e.g., X-Ray mammography or reflective or pulse echo ultrasound). Transmissive ultrasound with holography detection was able to differentiate gross as well as subtler variation among tissues and delineated the edges of breast structures, including cysts, ducts, fibroadenomas and cancers. It provides a whole breast field of view as well as acoustic zoom capabilities without loss of resolution. The real-time feature is important for guiding invasive procedures, such as biopsy.

A study was conducted at the University of Washington Medical Center in Seattle, Washington (with appropriate informed consent obtained from all participants) in 41 women to evaluate a transmissive ultrasound imaging technique with holographic image detection. The transmissive ultrasound and holographic imaging device was described in U.S. Pat. Nos. 5,212,571; 5,329,817; 5,179,455; 5,235,553; and 5,329,202 the disclosures of which are incorporated by reference herein and illustrated schematically in FIG. 1. The study first focused on resolving features within the breast of female volunteers with no known history of breast disease and then with patients with confirmed benign or malignant lesions. The confirmed disease category included women with positive mammograms, reflective ultrasounds or palpable masses.

The transmissive ultrasound device used three large area (77.4 cm$^2$) transducers. Two source transducers illuminated the object and one reference transducer was mixed with the transmitted beam. All operated at the same fixed center frequencies with ultrasonic output equalized over a 600 kHz bandwidth. The acoustic plane waves generated at the source transducers passed through the object (breast) creating a perturbed wave (altered through diffractions, reflections and refractions) which was received at the holographic detector apparatus. The reference transducer operated at a frequency matching that of one of the source transducers and produced an unpreturbed plane wave, which was also received by the detector. The interference pattern generated at the detector was illuminated with a laser and viewed using a CCD camera. The raw image was displayed on a high-resolution monitor for real-time viewing. There were three types of patient interfaces, which were interchangeable. In the first, the object of interest was immersed in a water bath that allowed dynamic positioning and simultaneous palpation and manipulation by the clinician. A second interface consisted of two water-filled bladders that were maintained in contact with the opposing sides of the object (breast) during imaging. Compression of the bladders against the breast was sufficient to hold the breast stable while contacting as much of the skin of the breast as possible to increase coupling area and the area viewed. The transmissive ultrasonic imaging allowed for scanning through layers of the breast tissue (i.e., the z axis) by progressively moving the focal plane and for acoustic zooming of the field of view via acoustic lens adjustment. The subjects were supported on a padded kneeling table that placed them in a semi-prone position. Baby oil was used as a skin-coupling agent. The chest was lowered until the breast was positioned between two water-filled pillows. Compression of the pillows against the skin completed the coupling. Scanning through the breast was completed by focusing from the lateral aspect of the breast to the medial aspect by acoustic lens adjustment. The images were acquired and viewed in real time and stored by video sequences on tape and as still images (provided in the figures herein).

Forty one patients or volunteers were studied with a mean age of 44. The study population consisted of 12 women with no lesions and 29 women with lesions. These lesions (confirmed by invasive means) included 25 masses (10 benign cysts, 10 fibroadenomas and 5 malignancies) and 4 calcification groups (3 benign and 1 representing ductal carcinoma in situ). Of the 12 women with no lesions, two had breast implants and two had ductal ectasia. Overall, the subjects' mammographic breast density was more dense than fatty, 81% demonstrated heterogeneously or extremely dense breast tissue, while 19% had scattered fibroglandular densities or almost entirely fatty breast tissue.

For a subset of benign and malignant lesions, there was a detailed comparative analysis of lesion characteristics on mammography, pulse-echo ultrasound (reflective ultrasound) and by the transmissive ultrasound described herein. The variables of maximum diameter, shape, margins and internal architecture was made. Mammographic breast density for all patients was rated using the American College of Radiology BI-RADS 4-point breast density characterization. For malignant lesions, specific histology and maximum diameter of the lesions were recorded from pathology. For benign masses, histology from core needle biopsies was recorded.

In normal women, transmissive ultrasound with holography imaging produced breast images showing structural features and normal tissue, such as nipple, skin line, subcutaneous fat, fibrous connective tissue and glandular tissue in all breast types. In particular, this technique was able to visualize clarity of ducts within the retroareolar complex and clear definition of the skin and subcutaneous tissue. Even in a patient with breast implants, compression to the breast and implant resulted in imaging the implant and surrounding breast tissue. The compression needed was much less than would have been needed for traditional mammography, a source of much patient discomfort.

The breast masses in the study population ranged in size from 4 mm to 5 cm with a mean of 1.8 cm. Transmissive ultrasound with holographic detection found septations and high contrast margins characteristic of benign fibroadenomas. Ten cysts were imaged wherein most were acoustically transparent (whiter gray level of display representing lower acoustical scattering) compared to adjacent breast tissue, but some appeared darker compared to surrounding tissue.

Figure 3A:
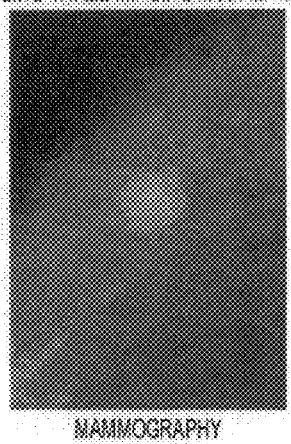
FIG. 3 shows comparative images of breast fibroadenomas using mammography (top left and bottom left), reflective ultrasound (top middle and bottom middle) and transmissive ultrasound with holography detection (called "optical sonography" and the top and bottom right images). The row of top images is a 2 cm fibrotic mass in a 47 year old female. In comparing the images from the three modalities it could be best sized from the transmissive ultrasound image. The bottom row is a 2–3 cm fibroadenoma in a 28 year old female. Again, it could be best delineated and could be best sized from the transmissive ultrasound image. In the mammography image, this lesion was not detected. However, in the case of this lesion, reflective ultrasound and transmissive ultrasound predicted the lesion of about the same dimensions.
Figure 3B:
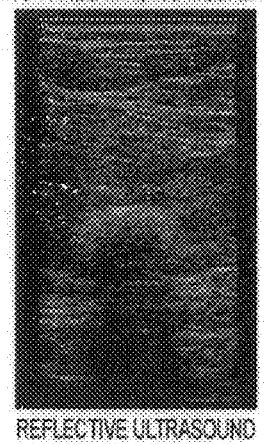
Figure 3C:
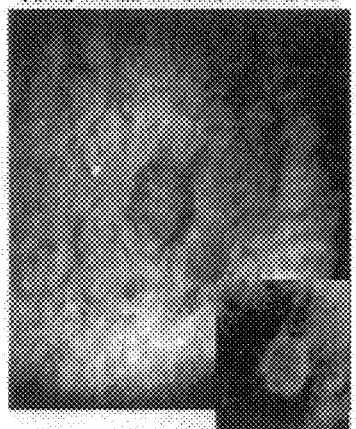
Figure 4A:
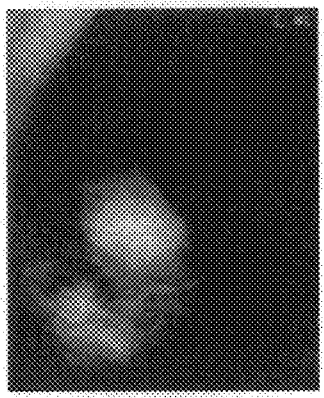
FIG. 4 shows comparative images of simple cysts using mammography (top left and bottom left), reflective ultrasound (top middle and bottom middle) and transmissive ultrasound with holography detection (called "optical sonography" and the top and bottom right images). The row of top images are 1–2 cm complex and simple cysts in a 38 year old female. It should be noted that only the transmissive ultrasound showed the multiple cysts, whereas the mammography image shows, at most, two cysts. It is most clearly delineated from the transmissive ultrasound image, although all the modalities showed a broad size range of 1–2 cm in diameter. The bottom row shows multiple 0.5 cm simple cysts in a 39 year old female. Again, it can be best delineated from the transmissive ultrasound image. Moreover, only the transmissive ultrasound image (as opposed to the X Ray or reflective ultrasound image) showed the most cysts.
Figure 4B:
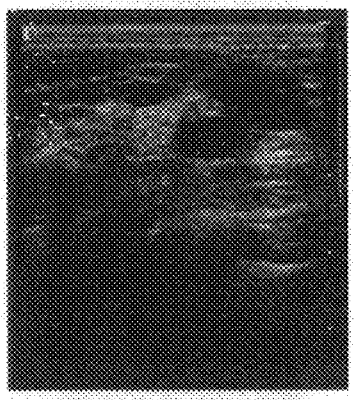
Figure 4C:
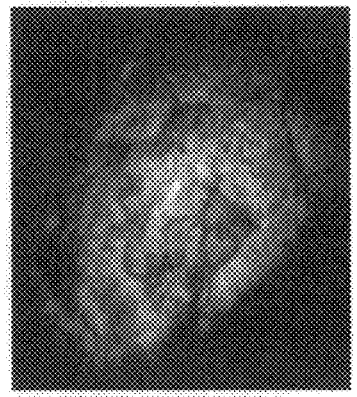
Figure 5A:
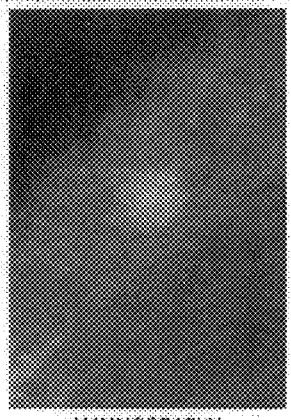
FIG. 5 shows in the top row of three images a 2 cm fibrotic mass in a 47 year old female comparing the three listed imaging modalities. Similarly, the bottom row shows a 2–3 cm fibroadenoma in a 28 year old female.
Figure 5B:
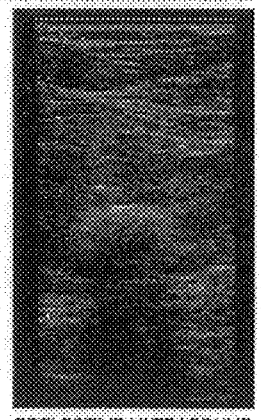
Figure 5C:
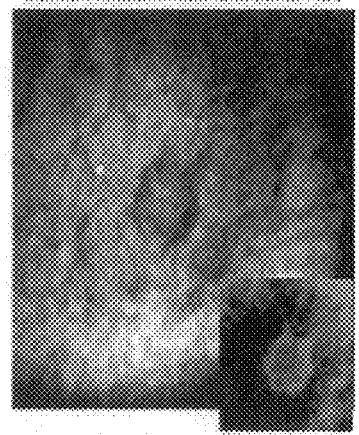
Figure 5D:
Figure 5E:
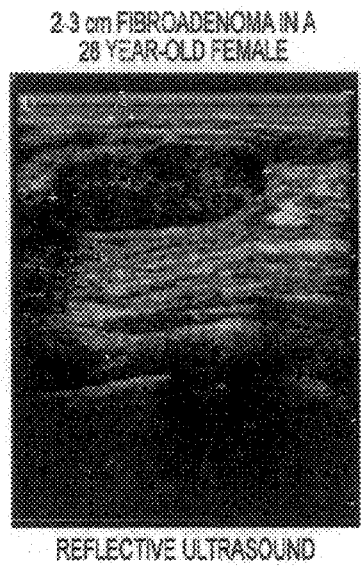
Figure 5F:
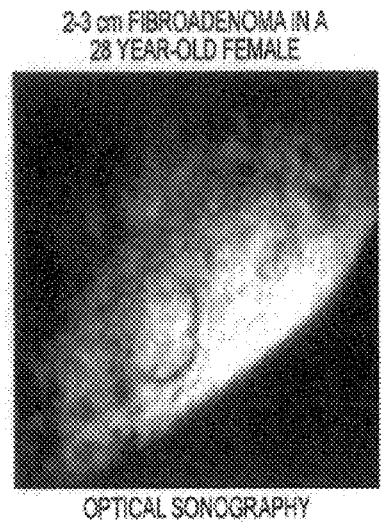

In Table 1 below, results from detailed comparative imaging analysis of three masses are compared. Mass 1 is a ductal infiltrating carcinoma (FIG. 2 top), mass 2 is a benign fibroadenoma (FIG. 3 bottom) and mass 3 is a cluster of benign cysts (FIG. 4 top). The pathology of surgically excised tumors documented invasive ductal carcinoma for mass 1. Mass 2 was diagnosed by histology from core needle biopsy samples. Mass 3 was diagnosed by fine needle aspiration under ultrasound guidance and resulted in complete collapse of simple cysts.

TABLE 1

| Lesion characteristics | Mammography | Reflective ultrasound | Transmissive ultrasound | pathology |
|---|---|---|---|---|
| Mass 1 | Not visible by mammography | 9 mm mass, round, indistinct, homogeneous, hypoechoic | 2.3 cm lobular indistinct, heterogeneous, dark | Invasive ductal carcinoma, 2.7 cm |
| Mass 2 | 2.0 cm oval indistinct, homogeneous, dense | 2.0 cm oval, indistinct, heterogeneous, hypoechoic | 2.0 cm oval indistinct heterogeneous, thick dark rim, light center | Fibroadenoma, not excised |
| Mass 3 | Multiple masses 1–2 cm, round, oval, circumscribed, obscured, homogeneous, dense | Clustered masses 1–2 cm, round, oval circumscribed, homogeneous, anechoic | Clustered masses 1–2 cm, round, oval circumscribed, Homogeneous, thin dark rim with light center | Benign cysts |

Two masses (one cancer, one benign fibroadenoma) were mammographically occult, even with retrospective review. In both cases, dense, overlying fibroglandular tissue completely obscured the masses on mammography. Both lesions were detected with both reflective ultrasound and transmissive ultrasound. In a mammographically occult cancer (mass 1), determination of the extent of tumor with reflective ultrasound was difficult. A 9 mm diameter mass was detected adjacent to a 1.6 cm ill-defined hypoecoic region. In transmissive ultrasound with holographic imaging, the lesion was seen as a central mass close to the chest wall with finger-like extensions protruding into the central breast tissue. The total abnormal area covered at least 2.3 cm with the most posterior edge of the mass not included in the field of view. On pathology following surgery, a 2.7 cm invasive carcinoma was confirmed.

For all benign lesions, maximum diameter measurements correlated well among all three modalities. However, the malignant masses always appeared to be larger with transmissive ultrasound with holographic detection (than either mammography if a lesion was detected or reflective ultrasound) and pathology reports following surgery confirmed that the tumor sizes most closely correlated with the measurement obtained by transmissive ultrasound as the preferred imaging modality. The comparative measurements of mass 1 are shown in Table 1. In other malignant masses, the maximum diameter was 3 cm by mammography and 2.6 cm by reflective ultrasound. The actual lesion was closer to 5 cm as determined by transmissive ultrasound. Pathology showed this lesion to be a 3.5 cm invasive carcinoma with multi-centric foci of tumor extending 1.7 cm beyond this primary lesion. Thus, the size determination by transmissive ultrasound was the most accurate.

Transmissive ultrasound with holographic detection requires an understanding of how to read the images displayed or recorded on various recording media. The internal architecture of the malignant masses tended to be heterogeneous with darker gray level (higher acoustical scatter) overall. The benign fibroadenomas tended to be homogeneously light centrally with dark rims (edge enhancements). Some of the dark rims were thin and well-defined while others were thick and microlobulated or indistinct. In most cases, cysts appeared relatively light internally (low scattering) with dark margins. However, there were cysts that appeared homogeneously darker compared with surrounding tissue. Larger microcalcifications were apparently detected on the transmissive ultrasound images corresponding to the same region in the breast on mammography.

What is claimed is:

1. A method for non-invasively determining dimensions of a lesion within soft tissue, comprising:
   (a) ultrasonically imaging soft tissue in an apparatus having an acoustic transducer, an acoustic focusing system, a holographic imaging detector, and a means for visualizing the holographic image;
   (b) obtaining a holographic planar image of a lesion in a first plane having a thickness z and having a dimension across a wide area of the lesion of x and a length across the lesion of y wherein y is at an approximately 90 degree angle to x;
   (c) determining if the image of the lesion is contained in different planar images;
   (d) measuring the x and y dimensions of the lesion in the plane having the largest sum of x plus y dimensions; and
   (e) determining the 3-dimensional size with a means for z-axis measurement.

2. The method of claim 1 wherein the soft tissue is breast tissue.

3. The method of claim 1 wherein the holographic planar image of a lesion in the first plane in step (b) uses all three axes to be orthogonal.

4. The method of claim 1 wherein the apparatus contains a holographic detector element for imaging in an optical mode the distortions cause by transmissive acoustic through the soft tissue.

5. The method of claim 1 wherein the means for z-axis measurement is to either determine numbers of planes traversed of a known thickness, or rotating the object (patient or body segment) such that the z-axis becomes a third dimension with an additional x-y axis measurement at about 90 degrees rotation, or both.

6. A method for guiding a biopsy device in soft tissue to a lesion, comprising imaging the soft tissue in an ultrasonic holographic apparatus having an acoustic transducer, an acoustic focusing system, a holographic imaging detector, and a means for visualizing the holographic image to simultaneously visualize both the biopsy device and the lesion site.

7. The method of claim 6 wherein the apparatus contains a holographic detector element for imaging in an optical mode the distortions caused by an acoustic wave being refracted, diffracted and reflected by structures with a soft tissue object.

8. A method for non-invasively determining dimensions of a lesion within soft tissue, comprising:

transmitting an ultrasonic wave through soft tissue;

focusing the through-transmitted waveform onto a detector surface to thereby select a focal plane within the soft tissue;

transmitting a reference ultrasonic wave onto the detector surface to thereby form a holographic planar image of the soft tissue;

visualizing the holographic image;

detecting a lesion in the imaged focal plane;

measuring an area of the lesion in the imaged focal plane;

altering the focal plane in the soft tissue to determine an area of the lesion in the altered focal plane and to determine a depth of the lesion; and calculating a three-dimensional size of the lesion.

9. The method of claim 8 wherein the soft tissue is breast tissue.

10. The method of claim 8 wherein the altered focal plane is substantially parallel to the imaged focal plane and the depth of the lesion is measured in a direction substantially orthogonal to the imaged focal plane and the altered focal plane.

11. A method for guiding a biopsy device in soft tissue to a lesion, comprising:

transmitting an ultrasonic wave through soft tissue;

focusing the through-transmitted waveform onto a detector surface;

transmitting a reference ultrasonic wave onto the detector surface to thereby form a holographic image of the soft tissue;

visualizing the holographic image; and simultaneously visualizing a lesion in the soft tissue and a biopsy device using the same ultrasonic waves to thereby guide the biopsy device.

* * * * *